US009433365B1

(12) United States Patent
Lin et al.

(10) Patent No.: US 9,433,365 B1
(45) Date of Patent: Sep. 6, 2016

(54) SYSTEM AND METHOD FOR INDENTIFYING ROTORS IN FRACTIONATED SIGNALS IN PERSISTENT ATRIAL FIBRILLATION ABLATION

(71) Applicant: National Yang-Ming University, Taipei (TW)

(72) Inventors: Yenn-Jiang Lin, Taipei (TW); Shih-Ann Chen, Jhongli (TW); Men-Tzung Lo, Jhongli (TW); Yi-Chung Chang, Jhongli (TW); Chen Lin, Johngli (TW)

(73) Assignee: National Yang-Ming University, Taipei (TW)

( * ) Notice: Subject to any disclaimer, the term of this patent is extended or adjusted under 35 U.S.C. 154(b) by 93 days.

(21) Appl. No.: 14/474,302

(22) Filed: Sep. 2, 2014

Related U.S. Application Data

(63) Continuation-in-part of application No. 13/558,616, filed on Jul. 26, 2012, now Pat. No. 8,862,213.

(51) Int. Cl.
*A61B 5/0402* (2006.01)
*A61B 5/046* (2006.01)
*A61B 5/04* (2006.01)

(52) U.S. Cl.
CPC ........... *A61B 5/04012* (2013.01); *A61B 5/046* (2013.01)

(58) Field of Classification Search
CPC ................... A61B 5/046; A61B 2018/00839
USPC ........................................ 600/509, 515, 518
See application file for complete search history.

(56) References Cited

U.S. PATENT DOCUMENTS

| | | | | |
|---|---|---|---|---|
| 5,035,144 | A * | 7/1991 | Aussel | G01N 29/075 73/602 |
| 5,868,680 | A | 2/1999 | Steiner | |
| 2002/0143479 | A1* | 10/2002 | Fukuhara | G01F 1/667 702/45 |
| 2009/0086618 | A1* | 4/2009 | Muschallik | H04L 27/2647 370/208 |
| 2010/0094274 | A1* | 4/2010 | Narayan | A61B 5/046 606/33 |
| 2010/0130873 | A1* | 5/2010 | Yuen | A61B 5/0205 600/484 |
| 2011/0015532 | A1* | 1/2011 | Koertge | A61B 5/0402 600/509 |

(Continued)

OTHER PUBLICATIONS

Xianzhao Yang, Gengguo Cheng, and Huikang Liu, "Improved Empirical Mode Decomposition Algorithm of Processing Complex Signal for IoT Application," International Journal of Distributed Sensor Networks, vol. 2015, Article ID 862807, 8 pages, 2015. doi:10.1155/2015/862807.*

*Primary Examiner* — Allen Porter, Jr.
(74) *Attorney, Agent, or Firm* — SV Patent Service

(57) ABSTRACT

A computer-assisted method for quantitative characterizing atrial fibrillation (AF) in a patient includes recording unipolar atrial fibrillation signals from multiple sites in a patient's atria, calculating bipolar electrograms using unipolar AF signals recorded at adjacent sites by a computer system, applying Empirical Mode Decomposition to remove a background from the bipolar electrogram signal to obtain a filtered bipolar electrogram signal, applying Hilbert transform to an envelope function of the filtered bipolar electrogram signal to obtain a time series of instantaneous phases of the filtered bipolar electrogram signal, and identifying a rotor region in patient's atria using the instantaneous phases in the filtered bipolar electrogram signal.

4 Claims, 22 Drawing Sheets

(56) References Cited

U.S. PATENT DOCUMENTS

| | | | |
|---|---|---|---|
| 2011/0040502 A1* | 2/2011 | Furmanski | A61M 1/3653 702/51 |
| 2011/0251505 A1* | 10/2011 | Narayan | A61B 5/0422 600/515 |
| 2013/0006131 A1* | 1/2013 | Narayan | A61B 5/042 600/508 |
| 2014/0088395 A1* | 3/2014 | Dubois | A61B 5/044 600/382 |
| 2014/0200575 A1* | 7/2014 | Spector | A61B 5/04014 606/40 |

* cited by examiner

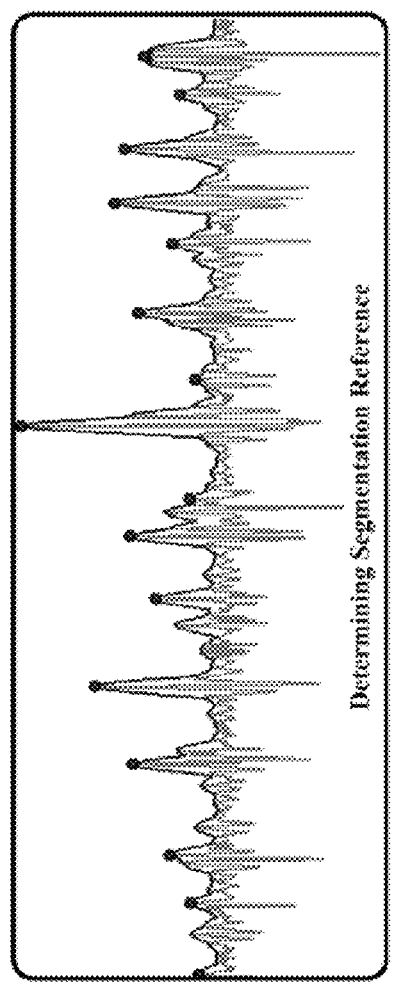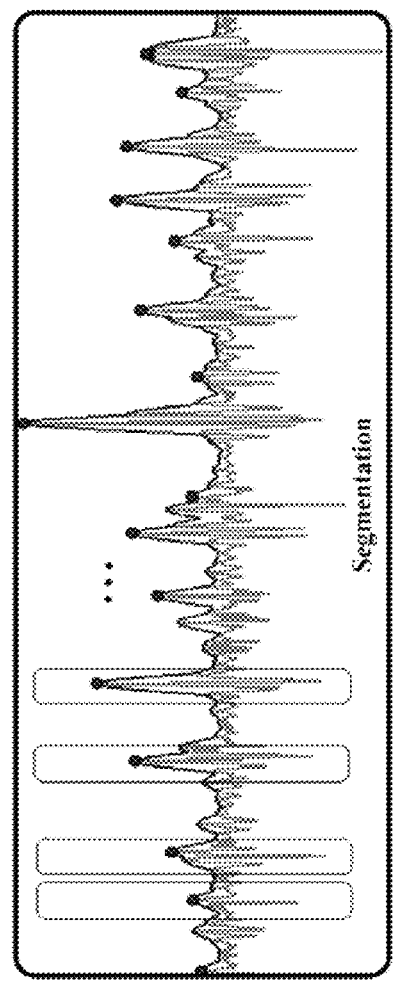
Figure 4D — Determining Segmentation Reference
Figure 4E — Segmentation

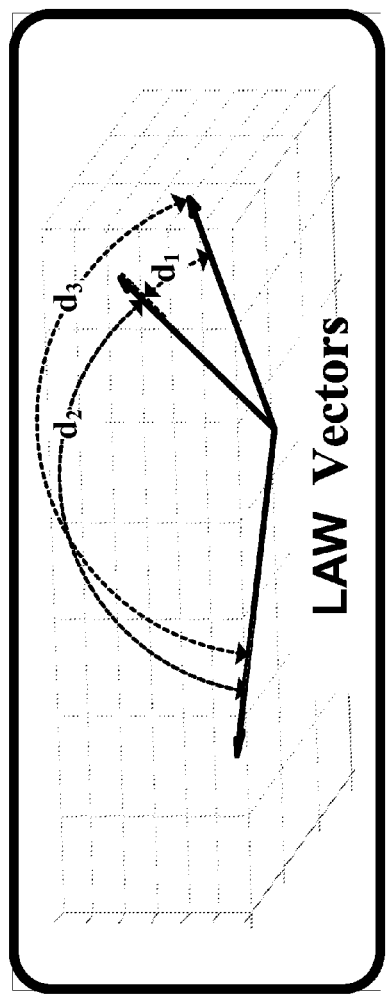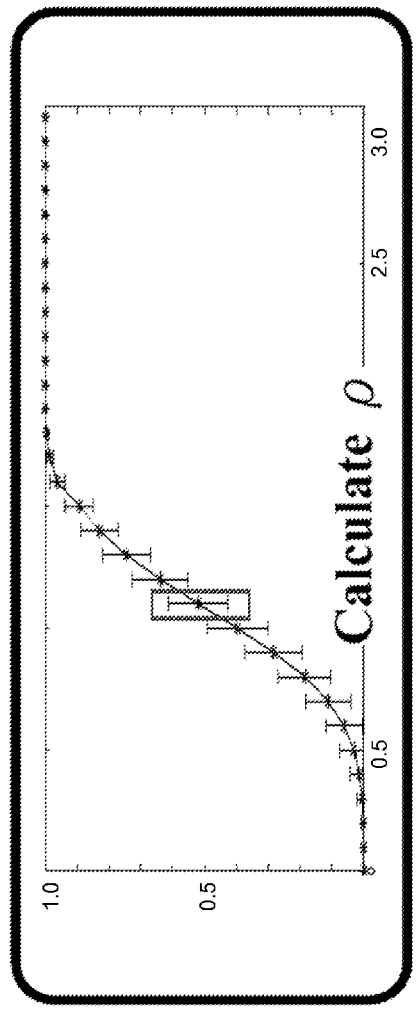
Figure 6A
Figure 6B

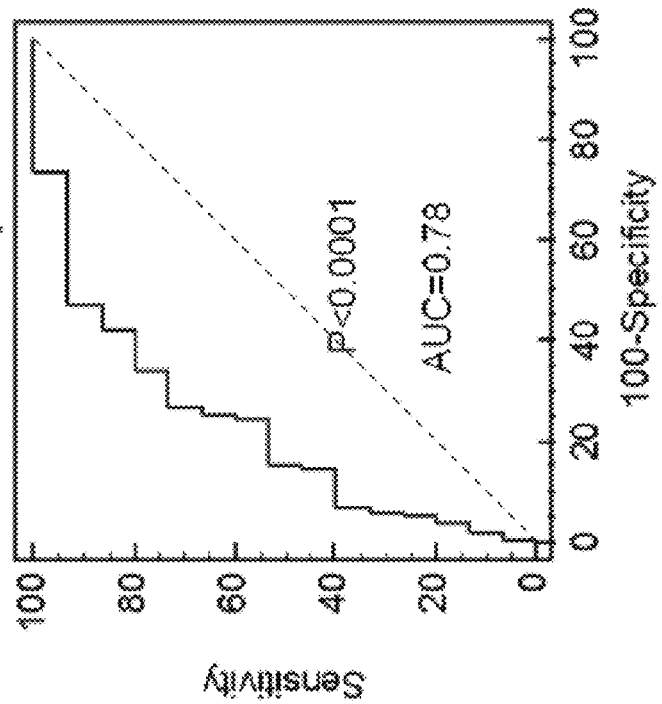
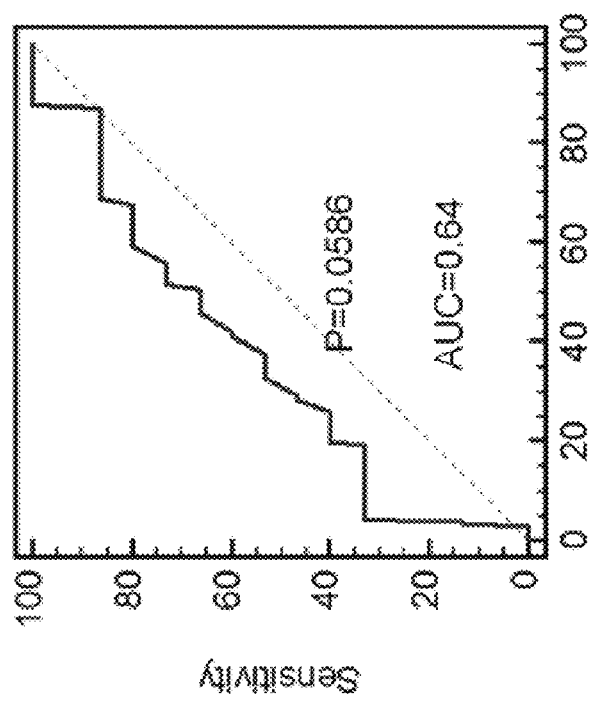
Figure 12A
Figure 12B

SYSTEM AND METHOD FOR INDENTIFYING ROTORS IN FRACTIONATED SIGNALS IN PERSISTENT ATRIAL FIBRILLATION ABLATION

BACKGROUND OF THE INVENTION

Atrial fibrillation (AF) is the most common type of tachyarrhythmia encountered in clinical practice. Catheter ablation is currently the standard therapy in patients who were refractory to antiarrhythmic medication. Pulmonary vein isolation (PVI) has become the mainstream catheter ablation technique for paroxysmal AF. For persistent AF, substrate modification with complex fractionated electrogram (CFE) ablation is considered to be necessary to patients who have not responded to PVI.

Conventional AF identification methods include dominant frequency (DF) analyses in frequency domain of consecutive electrograms, and CFE mean analysis in time domain of consecutive electrograms. Both methods produce average results based on activation intervals, which not applicable to diagnosing persistent or late stage AF patients. In particular, CFEs are usually observed in many regions of the atria, which make it difficult to identify critical atrial substrate using the conventional AF identification methods.

Recent clinical and animal studies have demonstrated that AF reentrant sources may be related to rotors, and the degree of electrogram similarity in the waveform propagating from the focal point can be a sensitive index for identifying the rotors.

For substrate mapping of AF, there is therefore a need to more accurate identification of critical regions and discriminate them from by-standers than conventional AF identification methods, especially, for accurate identification of rotor regions in persistent AF and facilitating electrophysiologist to search for the critical atrial substrate in maintaining AF.

SUMMARY OF THE INVENTION

The present application discloses an improved method for effectively identifying the substrate nature and localizing critical regions by more accurately analyzing atrial fibrillation signal from a patient. In contrast to conventional techniques that focus on the quantization of fractionality in the AF signals, the presently disclosed method is aimed to discover the repeating patterns among the fractionated AF signals as a way for enhancing the efficacy of catheter ablation and long-term outcome. For persistent AF, substrate modification with complex fractionated electrogram ablation is considered to be necessary in patients who have not responded to PVI. However, CFEs are usually observed in many regions of the atria, making identification of critical atrial substrate difficult. The presently disclosed method can discover regional disparities of the electrogram characteristics between the important CFE and the bystander CFEs which are difficult to identify by the interval analysis, dominant frequency value, and the temporal variation of the DF peaks (bandwidth of the DF peaks or the harmonic index in Fourier spectrum of AF signal). The presently disclosed method can differentiate those sites with repeating patterns from the bystander CFE and thus increase the rate of successful procedural AF terminations and long-term outcome after the first ablation procedure.

As described above, a rotor can be one of the significant mechanisms for AF maintenance in patients with persistent AF after PVI. Moreover, the repeating patterns could occur in the vicinity of the rotor. In the present disclosure, the indexes are validated to identify rotors from the real-time spatial distribution of phases estimated by Hilbert-Huang transform. Thus a new technique is developed to identify small-radius-reentry rotors in highly fractionated electrograms of patients with persistent AF.

In a general aspect, the present invention relates to computer-assisted method for quantitative characterizing AF in a patient. The method includes recording unipolar AF signals from multiple sites in a patient's atria; calculating bipolar electrograms using unipolar AF signals recorded at adjacent sites by a computer system; applying Empirical Mode Decomposition to remove a background from the bipolar electrogram signal to obtain a filtered bipolar electrogram signal; applying Hilbert transform to an envelope function of the filtered bipolar electrogram signal to obtain a time series of instantaneous phases of the filtered bipolar electrogram signal; and identifying a rotor region in patient's atria using the instantaneous phases in the filtered bipolar electrogram signal.

Implementations of the system may include one or more of the following. The step of applying Empirical Mode Decomposition can include decomposing a time series of the bipolar electrogram signal into a number of intrinsic mode functions; and removing intrinsic mode functions having frequency distributions below 1.5 Hz to obtain a filtered bipolar electrogram signal. The step of identifying a rotor region in patient's atria comprises: calculating a map of the instantaneous phases in the filtered bipolar electrogram signal in the patient's atria; calculating phase shifts at different positions around a center point relative to a phase at the center point, wherein the different positions are at substantially the same distance to the center point; and identifying a rotor in the patient's atria if the phase shifts at the different positions rotates around the center point. The step of identifying a rotor region in m patient's atria comprises: signal pre-processing and performing Hilbert transform to convert the signal; plotting time series of the instantaneous phases in the filtered bipolar electrogram signal recorded at the multiple sites in the patient's atria; and identifying a rotor in the patient's atria based on phase shifts at the multiple sites.

In another general aspect, the present invention relates to a computer-assisted method for quantitative characterization and treatment of ventricular fibrillation. The computer-assisted method includes: preprocessing, by a computer system, a time series of an AF signal obtained from a patient; segmenting the time series of the AF signal into activation segments by the computer system; obtaining local activation waveforms (LAW) from the activation segments; determining degrees of similarity between the LAWs; and identifying one or more critical regions in the patient's atria if the LAWs have degrees of similarity exceeding a first threshold value Implementations of the system may include one or more of the following. The activation segments can be identified based on maximum overlapping of the activation segments. The computer-assisted method can further include normalizing the LAWs in the activation segments before the step of determining degrees of similarity between LAWs. The computer-assisted method can further include calculating distances between different LAWs, wherein the degrees of similarity between LAWs are determined based on the distances between the different LAWs. The distances are calculated between successive LAWs and non-adjacent LAWs. Degree of similarity between two of the LAWs increases as the distance between the two LAWs decreases. The computer-assisted method can further include preprocessing the AF signal by applying order filters to the time series of the AF signal. The computer-assisted method can further include preprocessing the time series of the AF signal by band filtering before the step of applying order filters. The computer-assisted method can further include acquiring a time series of the atrial fibrillation signal from the patient.

In another general aspect, the present invention relates to a computer-assisted method for quantitative characterization and treatment of AF. The computer-assisted method includes identifying, by a computer system, deflections in a time series of the AF signal obtained from a patient; calculating a mean value of intervals between consecutive deflections in the AF signal; calculating Kurtosis value of a distribution of the intervals between the consecutive deflections in the AF signal; and identifying true complex fractionated electrogram areas if the mean value of the intervals is smaller than a first threshold, and if the Kurtosis value of the distributions of the intervals is larger than a second threshold.

Implementations of the system may include one or more of the following. The computer-assisted method can further include segmenting the time series of the AF signal into the activation segments before the step of obtaining local activation waveforms from the activation segments. The computer-assisted method can further include applying order filters to the time series of the AF signal before the step of segmenting. The computer-assisted method can further include preprocessing the time series of the AF signal by band filtering before the step of applying order filters. The computer-assisted method can further include obtaining local activation waveforms from the time series of the AF signal; determining degrees of similarity between LAWs; and identifying one or more critical regions in the patient's atria if the associated LAWs have degrees of similarity exceeding a third threshold value. The computer-assisted method can further include normalizing the LAWs in the activation segments before the step of determining degrees of similarity between LAWs. The computer-assisted method can further include calculating distances between the LAWs, wherein the degrees of similarity between the LAWs are determined based on the angles between the LAWs. The distances can be calculated between successive LAWs and non-adjacent LAWs. Degree of similarity between two of the LAWs increases as the distance between the two LAWs decreases.

Although the invention has been particularly shown and described with reference to multiple embodiments, it will be understood by persons skilled in the relevant art that various changes in form and details can be made therein without departing from the spirit and scope of the invention.

BRIEF DESCRIPTION OF THE DRAWINGS

The following drawings, which are incorporated in and form a part of the specification, illustrate embodiments of the present invention and, together with the description, serve to explain the principles of the invention.

FIGS. 4A-4E illustrate segmentation of the AF signal.

FIG. 6A shows angles between different pairs of LAW vectors. FIG. 6B shows cumulative distribution of similarity index (ρ) based on the angles between the LAW vectors and an optimal threshold in the cumulative distribution of the similarity index for determining termination sites within the continuous CFEs.

FIG. 12A is a plot of a receiver operating characteristic (ROC) curve showing a optimal threshold in detecting the termination sites within the continuous CFEs based on the algorithm of dominant frequency value.

FIG. 12B is a plot of a ROC curve showing optimal threshold in detecting the termination sites within the continuous CFEs based on the algorithm of the similarity index.

DETAILED DESCRIPTION OF THE INVENTION

Figure 1:
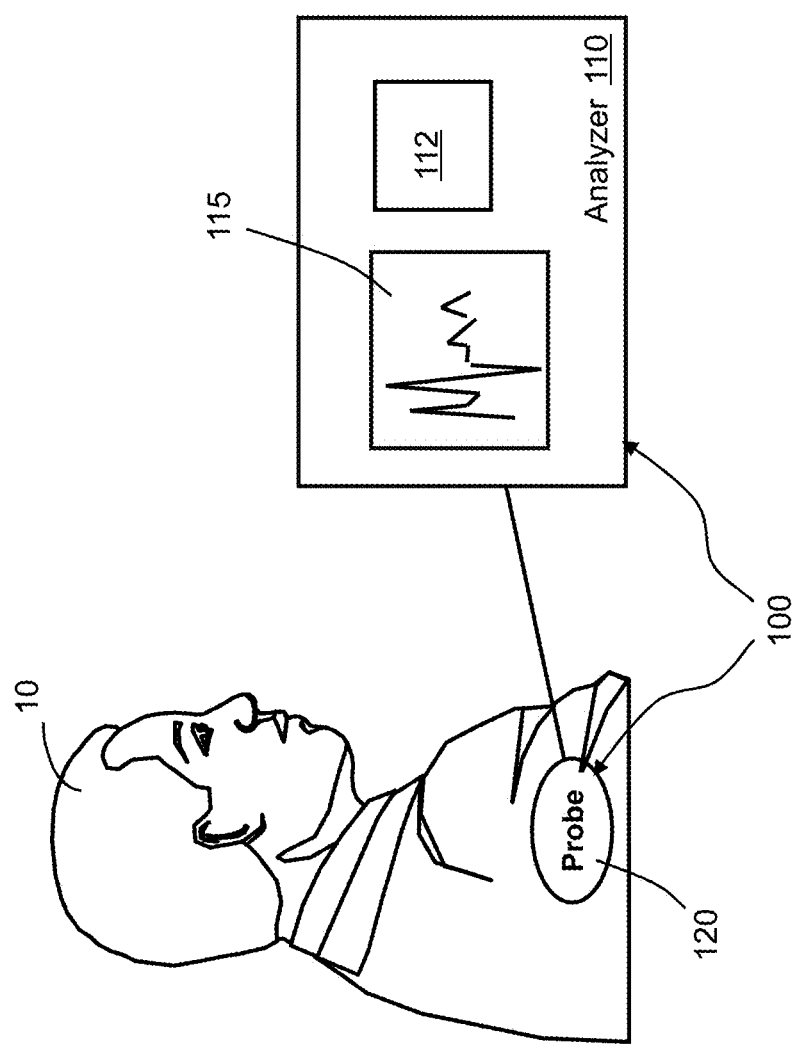
FIG. 1 is a schematic diagram of a system for evaluating atrial fibrillation (AF) in accordance to the present invention.

Referring to FIG. 1, an AF evaluation system 100 includes an analyzer 110 and a probe 120 that can be attached to a patient 10. The probe 120 can include a sensor, a transducer, or an electrode configured to measure intracardiac AF signals from the patient 10. The probe 120 can send the AF signals to the analyzer 110, often in analog form. The analyzer 110 can include an analog-to-digital (A/D) converter for digitizing the AF signals. The analyzer 110 also includes a computer processor 112 that is configured to process and analyze the AF signals after the AF signals are digitized by the A/D converter. A pre-stored algorithm in the analyzer 110 can rapidly analyze the AF signals, and provide guidance to defibrillation treatments, as described in more detail below. The analyzer 110 can also include necessary input/output devices, and a display 115 for displaying the AF signals and the results of the analysis of the AF signals.

Figure 2:
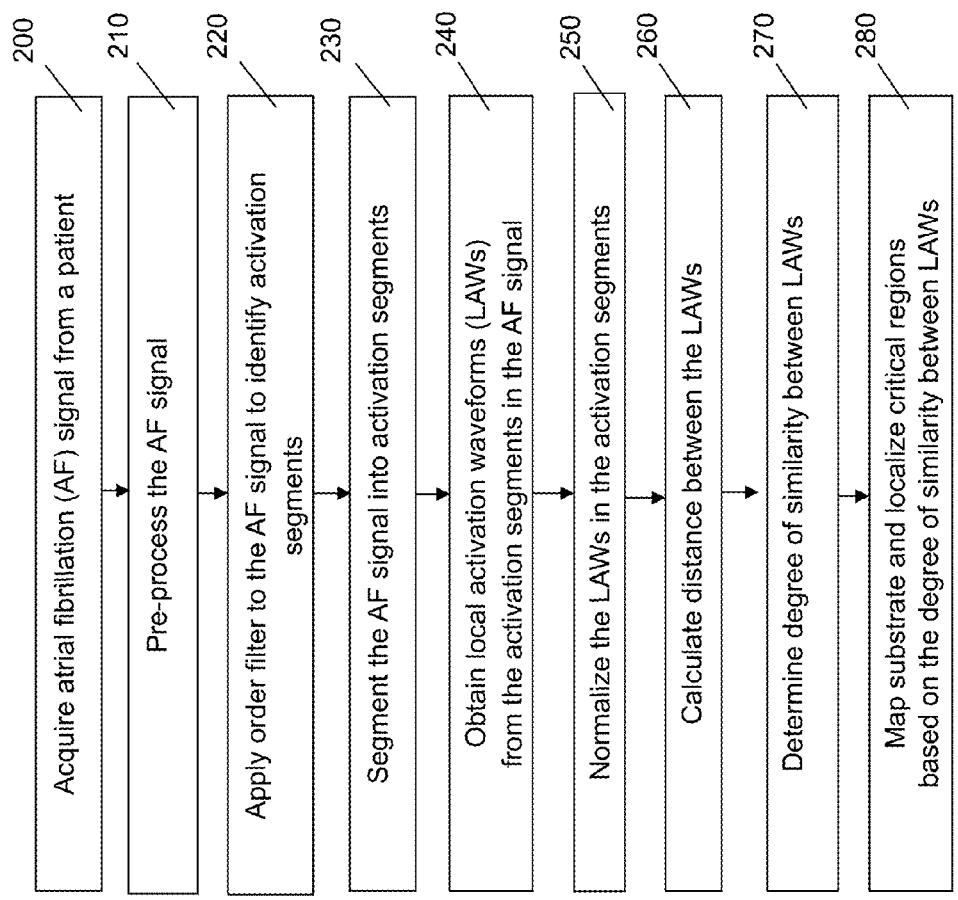
FIG. 2 is a flow diagram for processing and analyzing an atrial fibrillation signal to identify substrate nature and localize critical regions in patient's atria in accordance to the present invention.
Figure 3A:
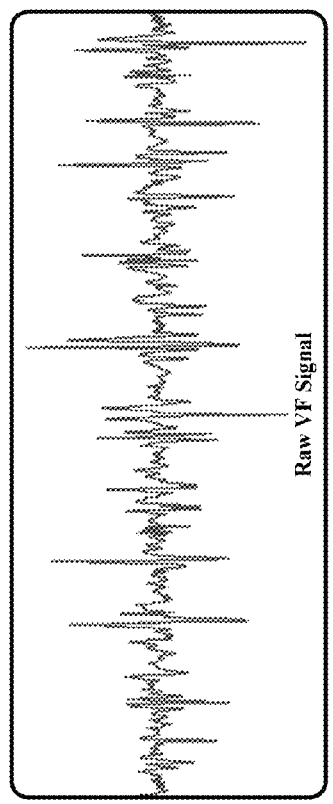
FIG. 3A illustrates a raw AF signal obtained by the system in FIG. 1.

In some embodiments, referring to FIG. 2, a process for analyzing a AF signal to identify substrate nature and localize critical regions include one or more of the following steps: a time series of a AF signal, shown in FIG. 3A, is recorded from a patient suffering from atrial fibrillation as described in relation to FIG. 1 above (step 200).

Figure 3B:
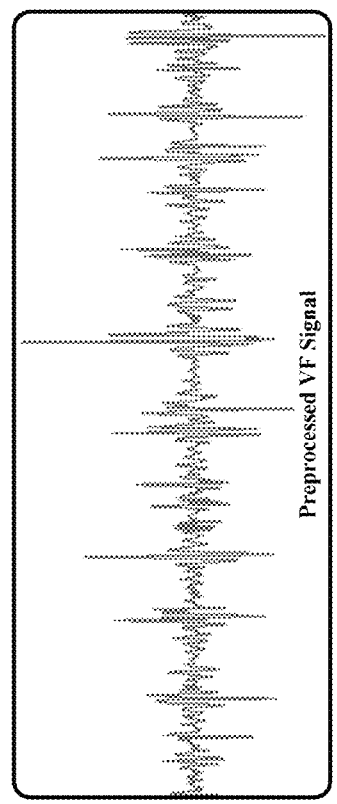
FIG. 3B illustrates pre-processing of the AF signal.

Optionally, the time series of AF signal is preprocessed (step 210). For example, as shown in FIG. 3B, the AF signal can be processed by band filtering to filter out high and low frequency noises.

Figure 4A:
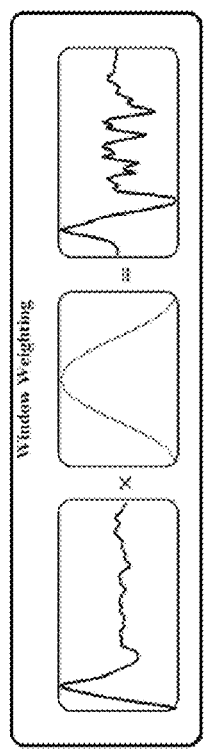
Figure 4B:
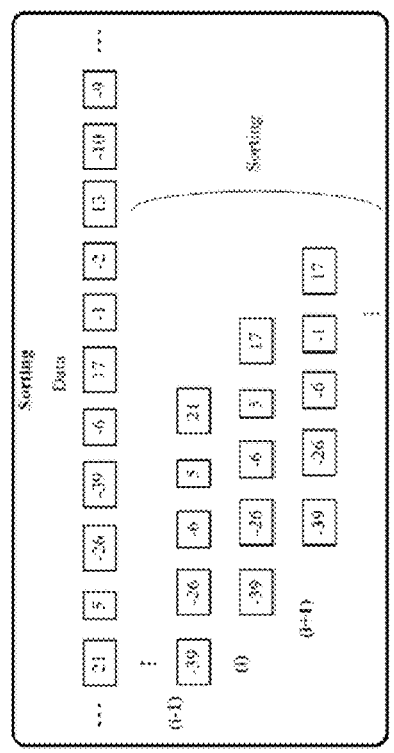
Figure 4C:
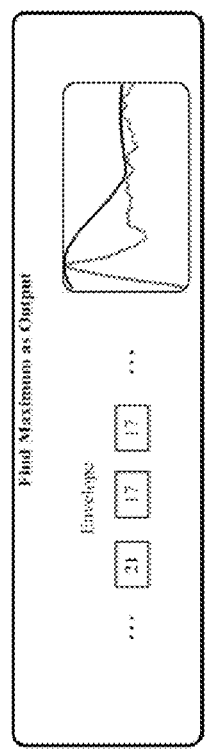

Next, referring to FIGS. 2 and 4A-4E, an order filter is then applied to the time series of AF signal (optionally filtered as described above) to identify activation segments (step 220). The time series of AF signal (the left curve in FIG. 4A) is weighted by a sliding window (the middle curve in FIG. 4A). The largest number among the weighted data (the right curve in FIG. 4A) within each sliding window is obtained as output. The window is shifted forward by 1-point each time and the procedure was repeated for each windowed data until the entire time series of AF signal is analyzed (FIG. 4B). After the envelope is obtained, the local activity peak is determined by finding the points with equal magnitude on the AF signal and envelope (FIG. 4C).

FIG. 4D shows the local activity peaks of the time series of AF signal. The time series of AF signal is segmented into activation segments based on the local activity peaks (FIG. 4E) (step 230). Details about the segmentation of the AF signal are described below in relation to FIG. 8. In some embodiments, the segmented windows in FIG. 4E can have the same widths for the different activation segments. For example, the window width can be set as 55 msec.

Figure 5A:
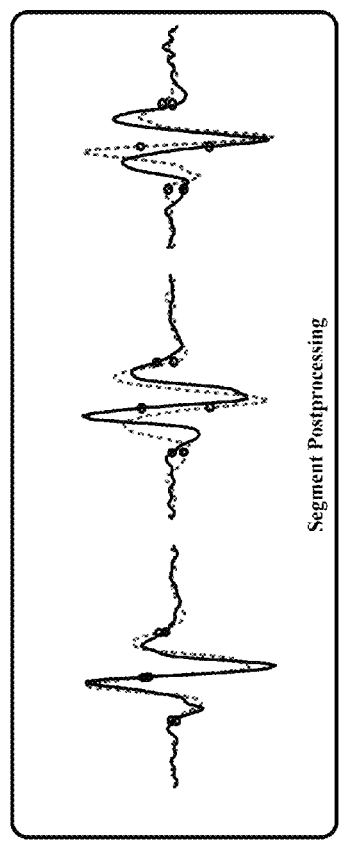
FIG. 5A illustrates local activation waveforms (LAWs) extracted from different segments and the post-processing of the LAWs.

Each segment includes a local activity waveform (LAW). A plurality of LAWs are cut out from the time series of AF signal as shown in FIG. 5A (step 240). The elements of each LAW $x_i$ (composed by m samples) can be regarded as a component of each dimension in an m-dimensional real space, and $x_i$ represented one point in this m-dimensional space.

Figure 5B:
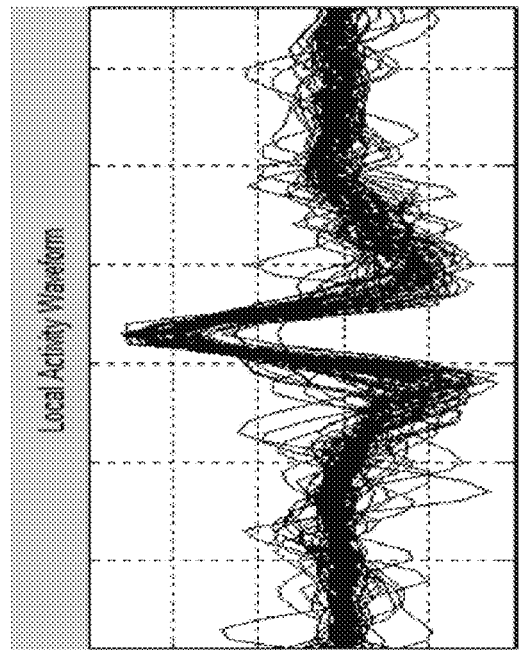
FIG. 5B shows normalized LAWs from different segments.

The segmented AF signal, as shown in FIG. 5A, is normalized (i.e. post-processing) (step 250). The normalized LAWs are shown in FIG. 5B. Each LAW was normalized to eliminate the variation of the amplitude of LAWs. Specifically, the normalization is achieved by dividing the LAW $x_i$ by its standard norm as denoted by $$s_i = \frac{x_i}{\sqrt{\sum_{j=1}^{m} x_{i,j}^2}} \tag{1}$$

where $s_i$ is the $i^{th}$ normalized LAW. Similar to the case of $x_i$ representing a point of the m-dimensional real space, the $i^{th}$ normalized LAW $s_i$ represents a point in the m-dimensional unitary sphere.

The distances between every pairs of LAWs (including adjacent and non-adjacent LAWs) were then defined by the standard metric of the sphere as given by $$d(s_i, s_j) = \cos^{-1}(s_i \cdot s_j) \tag{2}$$

where $s_i$ and $s_j$ represent the $i^{th}$ and $j^{th}$ normalized LAW and (•) denotes the scalar product. The distances between LAWs shown in FIG. 5B are calculated (step 260).

LAW vectors are constructed as illustrated in FIG. 6A. A similarity index (ρ) is then calculated based on the angles between LAW vectors (i.e. the distance between the associated LAWs). The similarity index (ρ) is inversely proportional to angle between LAW vectors (and to the distance between the associated LAWs). If the angle between LAW vectors of a pair of LAWs is smaller than a pre-determined threshold, this LAW pair is regarded as similar, and vice versa.

The similarity index ρ(ε) is defined as the ratio of the number of similar LAW pairs to the total number of LAW pairs in the analyzed recording $$\rho(\varepsilon) = \frac{2}{N(N-1)} \sum_{i=1}^{N} \sum_{j=i+1}^{N} \Theta(\varepsilon - d(s_i \cdot s_j)) \quad \Theta(x) = \begin{cases} 1, \forall x > 0 \\ 0, \forall x \leq 0 \end{cases} \tag{3}$$

In Equation (3), the parameter ε is an adjustable threshold. By comparing the distance between two LAWs derived in (2) to the threshold distance ε, we determined these two LAWs to be similar if the distance d was less than ε, or dissimilar if d was greater than or equal to ε. A concept illustration of the 3D case (i.e., m=3) is given in FIG. 6B which shows a cumulative distribution of similarity index (ρ). An optimal threshold ε can be determined in the cumulative distribution of similarity index (ρ) to determine degree of similarity between LAWs as (step 270). LAWs higher than the threshold in the cumulative distribution of similarity index (ρ) are considered as resembling each other.

For a given ε, the index ρ(ε) in (3) can be regarded to indicate the probability of finding similar LAW pairs in the analyzed AF electrogram. Although the values of the pre-defined parameters (e.g. ε and m, respectively representing the threshold distance and window length of LAWs) may alter the results of ρ, the values of ρ were similar within certain ranges of the values of pre-defined parameters by using peak alignment and for the best discriminative performance. In one non-limiting example, the window length of LAWs and ε are set to 50 msec and 1.1 respectively.

The resembling LAWs are mapped into substrate, as shown in FIGS. 7A-7D, which identifies critical regions (step 280). In the present application, the term substrate means the cardiomyocytes located in the region-of-interested of atria. Modification often means the ablation procedure perform on the substrate.

Figure 7A:
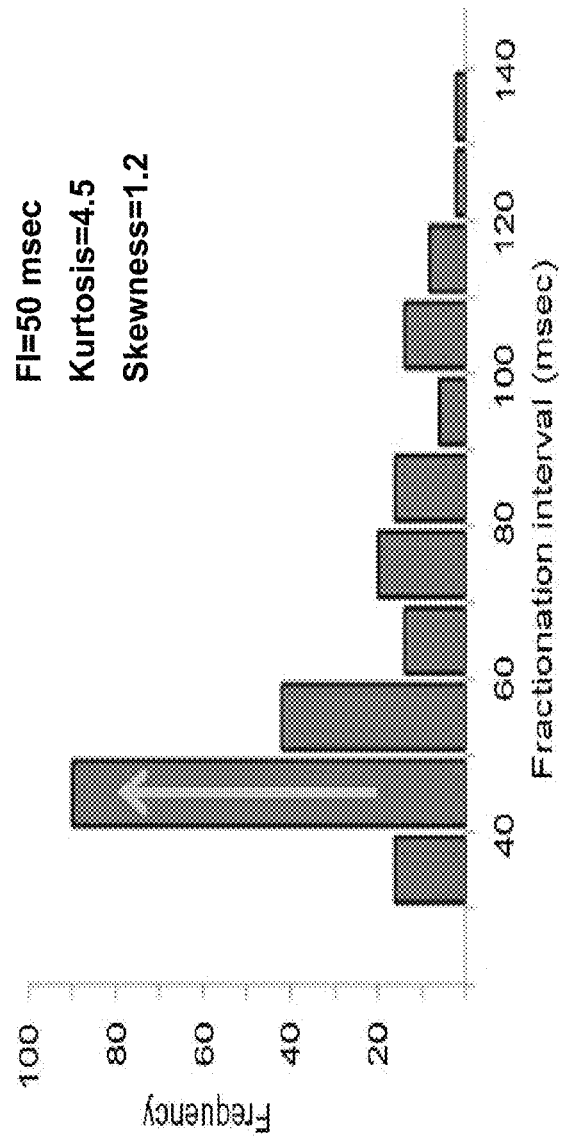
FIGS. 7A and 7B show histogram analysis of fractionation interval over 6 seconds at an AF termination site.
Figure 7B:
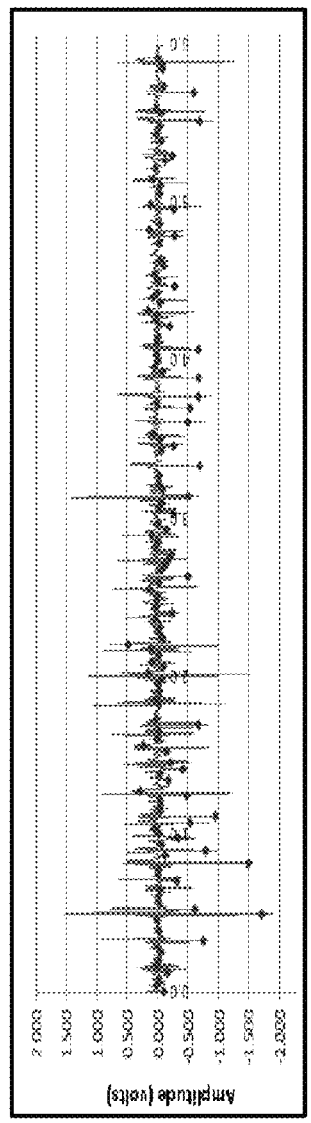
Figure 7C:
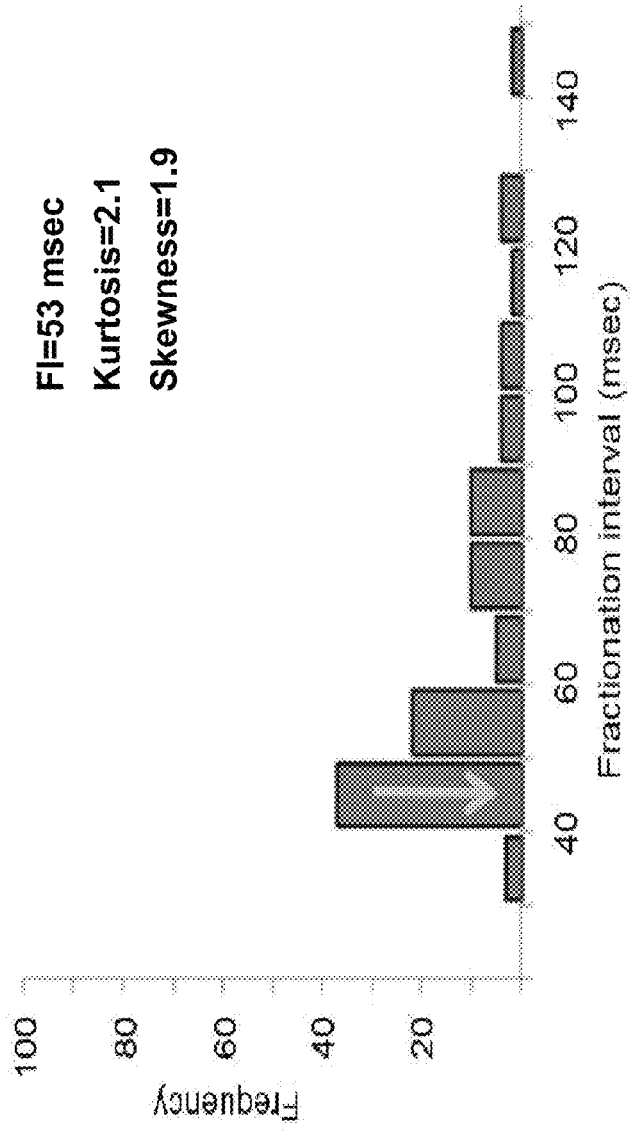
FIGS. 7C and 7D show histogram analysis of fractionation interval over 6 seconds at a continuous CFE site.
Figure 7D:
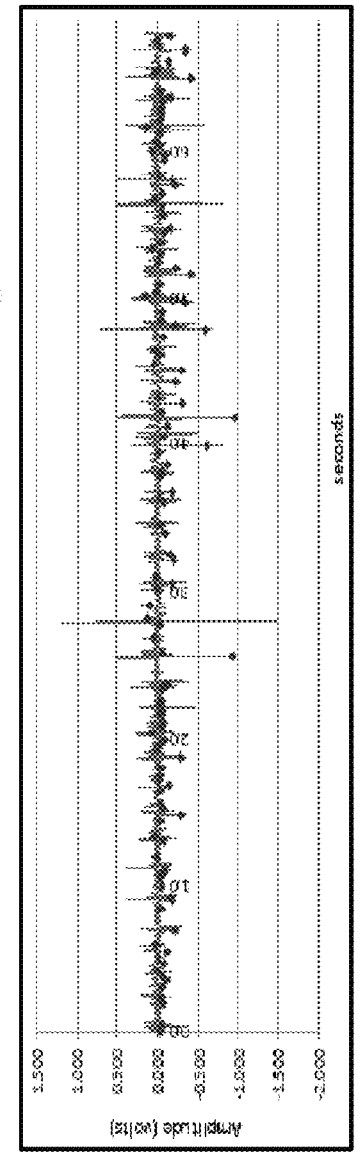

FIGS. 7B and 7D demonstrate the AF electrograms recorded from two different sites and the corresponding distribution of deflection intervals.

FIGS. 7A and 7B respectively show histogram and fractionation interval over 6 seconds at an AF termination site. The histogram (FIG. 7A) at this site exhibits a high kurtosis (of 4.5) with a sharp peaked distribution and positive skewness. This site exhibited a continuous fractionated signal of 50 msec.

FIGS. 7C and 7D show histogram analysis and fractionation interval over 6 seconds at a continuous CFE site. The histogram (FIG. 7C) at this site exhibits a low kurtosis (of 2.1) and positive skewness, whereas this site exhibits a continuous fractionated signal of 53 msec. CFE-targeted ablation at that site did not terminate AF.

Although mean values of the distribution of interval deflections for the two sites described above are similar (50 msec vs. 53 msec), but their Kurtosis values are quite different (4.5 vs. 2.1). It is discovered in the present invention that that the ablation on the site with high kurtosis can terminate the AF.

As described above, for longer duration AF, substrate modification with a complex fractionated electrogram ablation is considered to be necessary in patients who do not respond to PVI. The development of automated analysis algorithms for electrogram fractionation is important for a reproducible and objective assessment of this technique. However, most of the algorithms have been based on the mean fractionation interval (FI) between the deflection of the time-domain electrograms, such as the CFE-mean of the NavX system or shortest complex interval of the CARTO system. Detection is based on 3 criteria, set by the user, in which the deflection must: (1) exceed an adaptive peak-to-peak sensitivity threshold that is set at a reference-amplitude slightly greater than the baseline noise; (2) possess a downstroke morphology for which the leading maximum and trailing minimum amplitudes occur within a time duration that is set to minimize the detection of broad, far-field events; and (3) exceed a refractory period after the previous detection that is set to minimize multiple detections on a single deflection event. The variation in the FIs acquiring by those modalities may be important for the interpretation of the substrate characteristics. Therefore, if the local FIs are not normally distributed, there is a limitation of the mean FI with a clinical application due to the temporal variation.

The present application discloses that the temporal variation in the annotated FI can provide important information to determine the features of critical CFEs in addition to the conventional FI algorithm. i.e., the local consistency of the fractionated electrograms can be assessed according to the distribution of FIs for a recording duration. The assessed electrograms in each patient were acquired and characterized by the "kurtosis" of the FI distribution. Briefly summarized, kurtosis measures the shape of distribution of the fractionated intervals within the window beyond simply using their mean or standard deviation. The value of kurtosis gives the relationship between each of the FIs to their mean. The higher the value of kurtosis, the less probable that FIs deviate from their mean.

Figure 8:
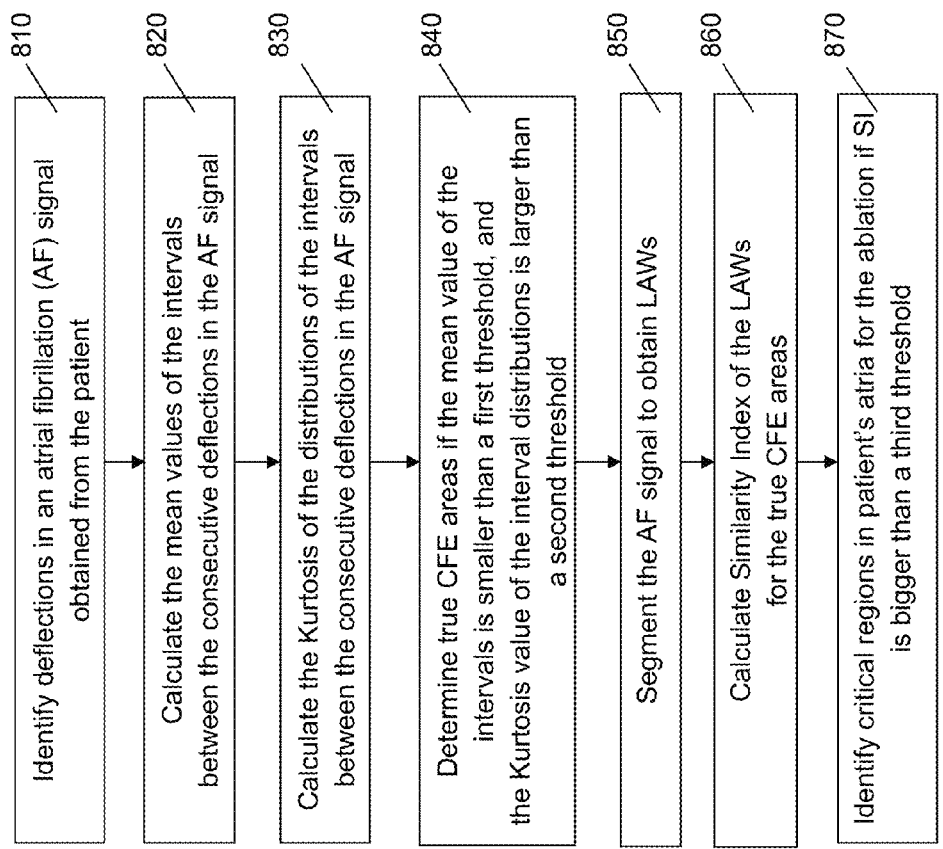
FIG. 8 is a flow diagram showing detailed steps of segmenting an atrial fibrillation signal to identify critical regions in patient's atria in accordance to the present invention.

In some embodiments, referring to FIG. 8, the presently disclosed method identifies critical regions (i.e. the "crucial" or "true" CFE) and discriminates them from by-standers by one or more of the following detailed steps: deflections in an AF signal are identified (step 810). The intervals between the consecutive deflections are calculated. The mean value of the intervals is calculated (step 820). The Kurtosis of the interval distributions is calculated (step 830). True CFE areas for the ablation are determined based on the criteria: mean value of the intervals is smaller than a first threshold, and the Kurtosis value of the interval distributions is larger than a second threshold (step 840).

In some embodiments, the operation accuracy can be further improved by segmentation steps as described in FIG. 2. The time series of the AF signal can be segmented into activation segments to obtain LAWs, as described above (step 850). Similarity index between LAWs is calculated for the areas identified (step 860). The critical regions in the patient's atria for the ablation are identified if SI is bigger than a third threshold (step 870).

If the areas which are identified as the true CFE are still extensive, the present disclosed method further identifies critical regions and discriminate them from by-standers, the presently disclosed method evaluates characteristics of a region by more accurately analyzing AF signal including: an elaborative segmentation to the AF signal and quantitative assessment of the repeating patterns in AF signal.

Mechanistic Considerations

The above described process is based on the following mechanistic considerations: Previous studies demonstrated the efficacy of adjunctive CFE ablation in addition to circumferential PVI. Considering that CFEs may play an active role in persistent AF, a CFE that maintains AF should be continuous and stable over time. Based on the time-domain signal, catheter ablation at sites displaying a greater percentage of continuous activity was associated with slowing or procedural AF termination (successful stop of AF) by catheter ablation in chronic AF. In recent years, automatic algorithms for 3D mapping systems have provided a rigorous quantitative analysis enabling the identification of the continuous CFEs and stability of the CFE distribution over time.

Mathematically, the morphological change over the distribution of the deflection types, total duration of the discrete electrograms, and intervals between consecutive deflections within the segmented windows, all contributed to the measurement of the stationarity feature of the electrograms. To non-paroxysmal AF patients, it is important to differentiate the culprit CFEs from the bystander CFEs. The stability of the electrograms may also reflect the presence of a focal pattern of activation.

Assuming consistent wavefront dynamic and activation patterns are emanating from the AF sources, repetitive waveforms of similar electrogram morphology should appear near the potential AF maintainers. A higher level of the electrogram similarity index over time at the continuous CFEs was more likely to respond to substrate modification. This can provides an alternative mapping tool to guide substrate modification.

Validation

One hundred consecutive persistent AF patients that received catheter ablation have been studied using the method described above. A total of 9558 fibrillatory electrograms were analyzed in this study (139±30 sites per patient in LA).

Substrate Mapping of the Global Atria

Figure 9A:
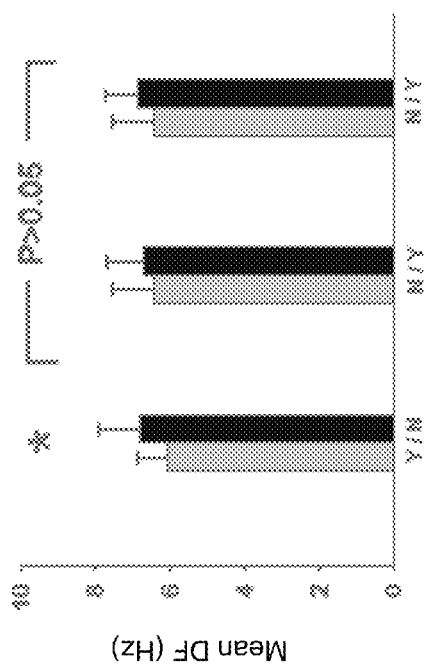
FIG. 9A shows the use of mean dominant frequency of the left atrium for predicting AF procedural termination, recurrence after the first ablation procedure, and recurrence after the final procedure.

FIG. 9A shows mean dominant frequency of the left atrium for predicting AF procedural termination, recurrence after the first ablation procedure, and recurrence after the final procedure. The phrase "procedure termination" means successfully stop the AF by catheter ablation. The phrase "recurrence after index" means the AF occurs again in some specific duration (e.g., in a month or half year). The phrase "final recurrence" means although AF disappears during the duration above, it occurs finally.

Figure 9B:
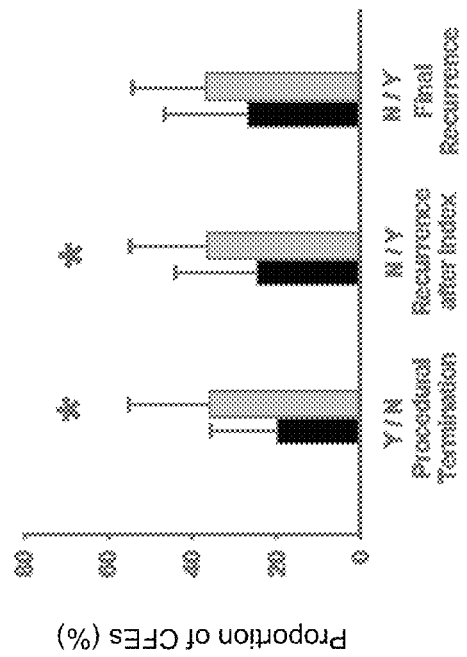
FIG. 9B shows the use of proportion of the continuous CFEs of the left atrium for predicting AF procedural termination, recurrence after the first ablation procedure, and recurrence after the final procedure.

FIG. 9B shows proportion of the continuous CFEs of the left atrium for predicting AF procedural termination, recurrence after the first ablation procedure, and recurrence after the final procedure. In FIGS. 8A and 8B, the * symbol means the discriminant performance is successful and reliable. "Y" and "N" respectively mean "True" and "False".

FIGS. 9A and 9B show comparisons of electrogram characteristics of the entire left atrium in the patients who did and did not respond to CFE ablation in terms of procedural AF termination and long-term AF recurrence (efficacy of single and multiple procedures without drugs). Patients with atrial substrate characteristics harboring rapid activity and more fractionated electrograms are less likely to respond to CFE ablation, as indicated by a higher DF (dominant frequency) (P>0.05), and higher proportion of CFEs in the left atrium (P<0.01), wherein the p-value is defined as the probability of obtaining a test statistic at least as extreme as the one that was actually observed.

To identify possible target of ablation, previous studies used the dominant frequency (DF) and the location with highest DF as the target. However, FIG. 9A shows that for all the recurrence patients, DF value (The "first generation method") has a P-value larger than 0.05 and is no longer effective for discrimination.

FIG. 9B illustrates the proportion of continuous CFE can be a better index for discriminating/predicting the results, whether the P-value is larger than 0.05 or not is critical. FIG. 9B also shows that continuous CFE (the "second generation method") is somehow effective since the proportion of continuous CFE become higher on persistent patients, but we obviously cannot ablate all the substrate with continuous CFE. So there is a need for an improved method to better identify the ablating target.

Correlation of Ablation Outcome and Electrogram Characteristics

Figure 10A:
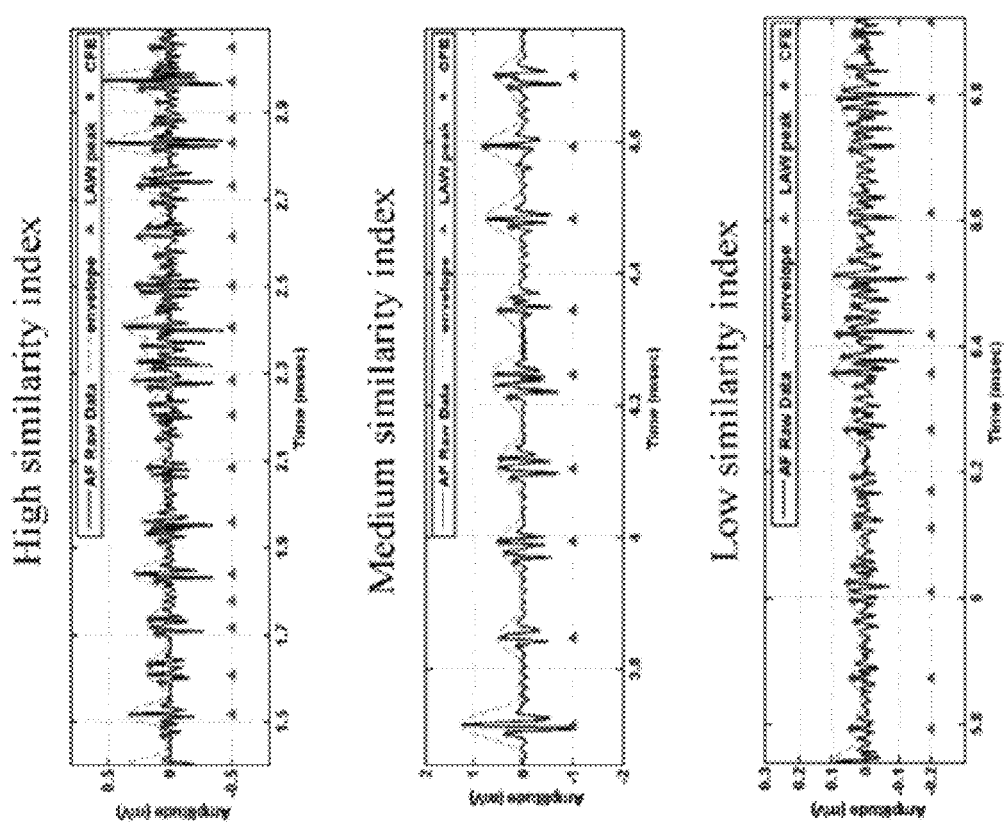
FIG. 10A show continuous complex fractionated electrograms having different similarity indices.
Figure 10B:
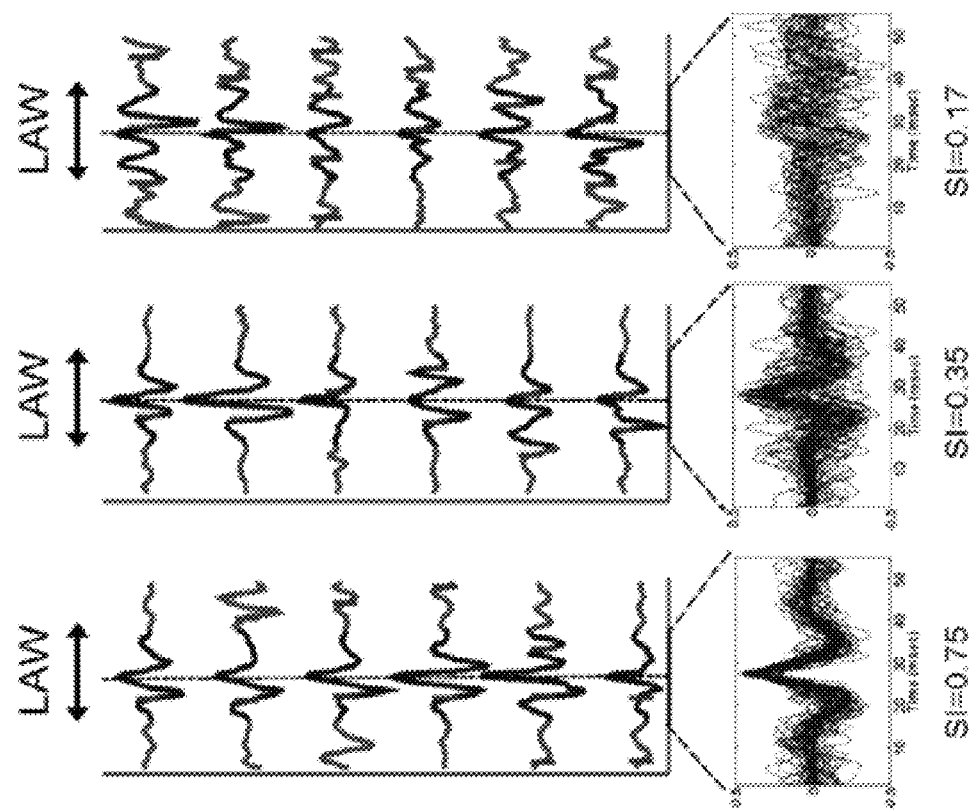
FIG. 10B shows LAWs respectively obtained from the complex fractionated electrograms in FIG. 10A.

FIGS. 10A and 10B show analysis of the electrogram similarity with different types of continuous complex fractionated electrograms (CFE). FIG. 10A shows exemplified bipolar fractionated electrograms including rapid activity and continuous electrograms with high, medium and low similarity indices. The envelop function of the filtered data (dotted line) and start points of the CFE deflections (triangle) are shown. Each LAW consists of multiple deflections and some of those might be CFE deflections. FIG. 10B shows LAWs obtained from the electrograms with high, medium and low similarity indices in FIG. 10A. The normalized electrograms of all the LAWs overlap with their center peaks and corresponding similarity index. Note that in addition to the high morphological similarity of the LAWs in the high similarity site, the CFE deflections (triangle label) are temporally well aligned.

The averaged similarity index of the targeted CFEs was higher in terms of procedural termination and AF recurrence. A disparity of the similarity was not observed in the non-continuous CFEs (0.51±0.09 vs. 0.51±0.11, P=NS) and non-CFEs (0.41±0.13 vs. 0.44±0.11, P=NS, in the patients with and without termination, respectively.

In patients with procedural termination, the termination sites (N=27) were characterized by a significantly higher similarity index compared to the other ablation sites (0.65±0.086 vs. 0.56±0.076, P=0.0001).

Figure 11A:
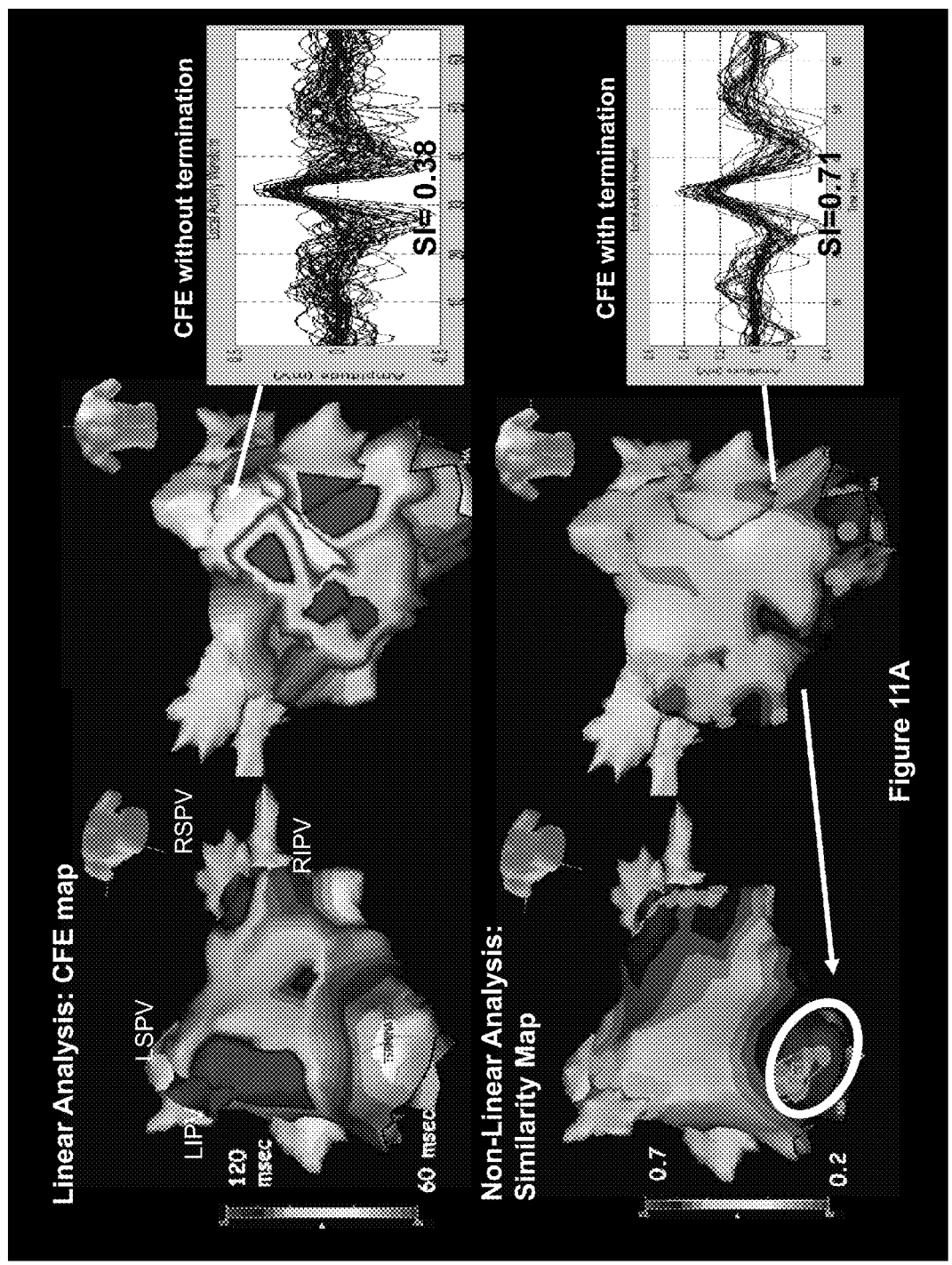
FIG. 11A shows exemplified 3D similarity map and fractionation map in patients with procedural AF termination.
Figure 11B:
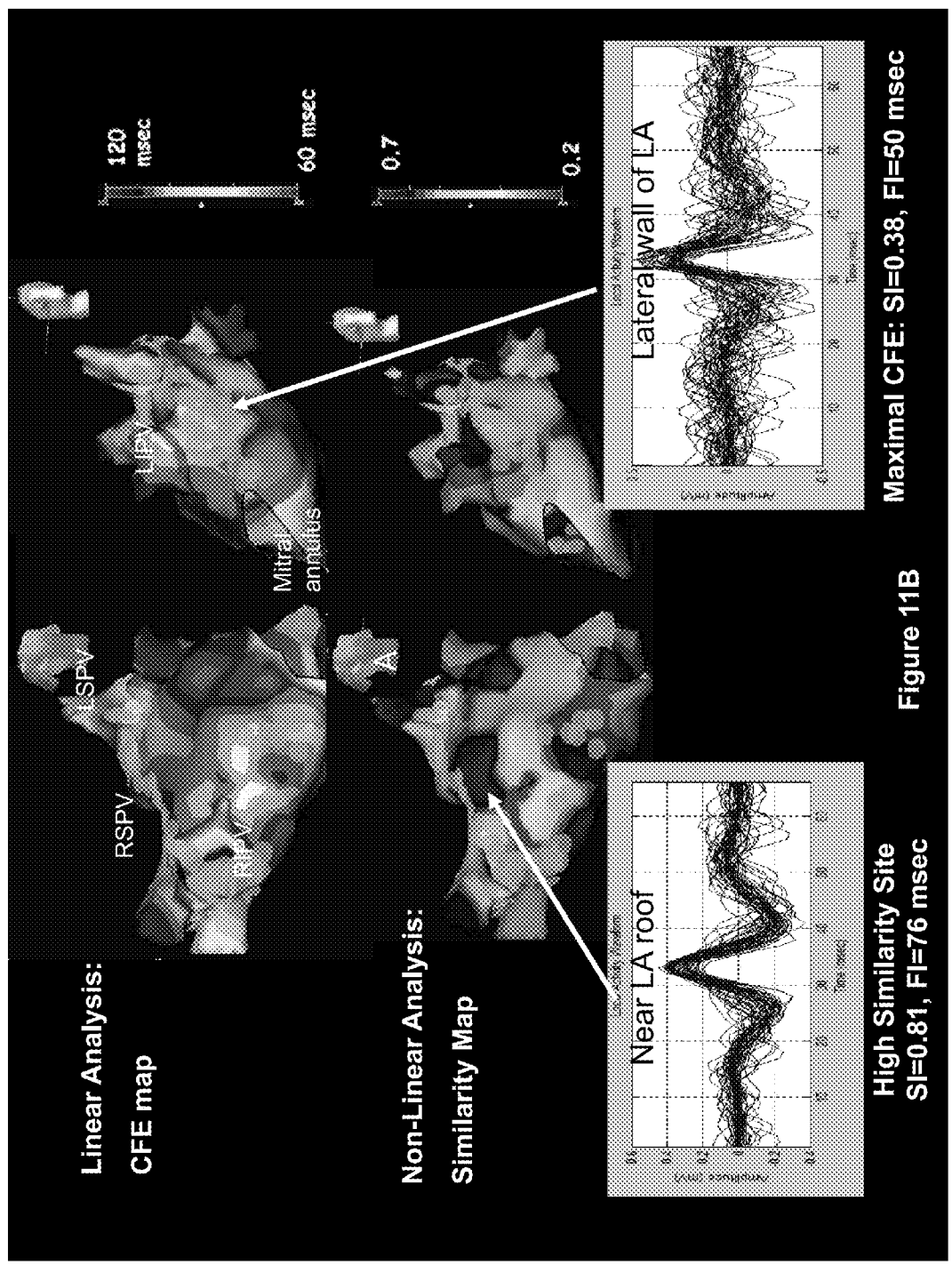
FIG. 11B shows exemplified 3D similarity map and fractionation map in patients without procedural AF termination.

FIGS. 11A and 11B show examples of 3D similarity map and fractionation map in a patient with and a patient without procedural AF termination. FIG. 11A shows an example of procedural AF termination at the posterolateral LA, where the high level of SI was compatible with the maximal CFEs. In contrast, in FIG. 11B, maximal CFE ablation in the lateral mitral annulus and LA septum could not terminate AF. Subsequent roof line ablation (with a mean FI of 76 msec, SI=0.81) terminated AF without AF recurrence during long-term follow-up.

In FIG. 11A, the maximal fractionated sites were identified with the high similarity index in the lateral mitral isthmus region. The similarity index locally was 0.71, whereas the similarity index of the CFEs in the anterior wall was 0.38. In contrast, in FIG. 11B, the maximal CFE ablation in the lateral mitral annulus and LA septum could not terminate AF. The maximal CFE was not associated with the high similarity index. The highest similarity near the border of the continuous CFEs was identified in the roof region. In this patient, ablation in the roof region terminated the AF with final SR maintenance during the long-term follow-up. A subsequent roof line ablation (with a mean fibrillation interval of 76 milliseconds, SI=0.81) terminated AF without any AF recurrence during the long-term follow-up.

The Optimal Detection Algorithm for CFEs

Within all the CFE regions (FI <120 msec), a univariate analysis showed that both a shorter mean FI and higher SI were associated with procedural AF termination. The DF value, HI value, and electrogram voltage did not correlate with the termination (P>0.05). A multivariate regression analysis showed that only a higher SI (≥0.57, Odd ratio=4.9, 95%, the confidence interval CI=1.33-18.0, P=0.017) predicted procedural AF termination. Sites with a shorter mean FI did not predict procedural termination (<70 msec, odd ratio=1.69, 95% CI=0.61-4.67, P=0.31).

We analyzed the predictors of the signal characteristics from the procedural termination sites (N=27), and non-terminating ablation sites in patients with and without procedural AF termination (N=7438). FIG. 12A is a plot of a receiver operating characteristic (ROC) curve showing the optimal thresholds in detecting the termination sites within the continuous CFEs based on the algorithm of dominant frequency (DF) value. The ROC curve analysis shows an optimal cut-off threshold value of the DF>10.2 Hz within the continuous CFEs correlated with the termination with a sensitivity of 0.35 (0.12-0.62) and specificity of 0.93 (5% CI=0.90-0.94).

FIG. 12B is a ROC curve showing the optimal threshold for detecting termination sites within the continuous CFEs based on the algorithm of the similarity index. This ROC curve analysis shows an optimal cut-off threshold value of the SI ≥0.565 within the continuous CFEs correlated with the termination with a sensitivity of 0.73 (95% CI=0.45-0.92) and specificity of 0.73 (5% CI=0.72-0.74, area under curve=0.781, P<0.001).

On the contrary, using the higher DF value to predict the termination sites was difficult (Cut-off value=10.2 Hz, sensitivity of 0.33 (0.12-0.62), specificity=0.95-0.96, area under curve=0.64, P=0.0586, as shown in FIG. 11A). Thus the disclosed CFE method is a much better predictor than DF for termination site predictions.

The disclosed system and methods can include one or more of the following advantages: within the continuous CFEs, a conventional linear signal analysis could not differentiate the termination sites from non-termination sites. The sites with a high level of fibrillation electrogram repetitiveness at the CFEs are important for AF maintenance. The proposed analysis rules 1) proper segmentation and 2) stationarity evaluation to the consecutive fibrillation electrograms can serve as an effective tool for distinguishing the culprit CFEs from the bystander CFEs in patients with persistent AF, and further refine the current substrate modification procedure.

Identifying Rotor Regions in Persistent AF

In some embodiments, after the steps 210-280 shown in FIG. 2 and FIGS. 3-12B, rotors with fibrillatory conduction in the atrial substrate can be characterized by rapid repetitive activity with a high degree of similarity in the fibrillatory electrograms. The similarity index is used to predict in which critical region the rotor can possibly be present. Multi-probe-type catheter can simultaneously record data from several sites to obtain both spatial and temporal information. Such information can help to characterize the electrical properties of the atrial substrate as well as the pathogenic mechanism which are useful for identifying the culprit location of atrial fibrillation and determining the strategies for ablation. To show localized sources of AF in the form of rotor maps, the computational maps were analyzed to identify rotor regions. In which, rotors are defined as rotation activity around a center. When wavefront with anatomical or functional obstacle interacts, the spiral wave will happen, which leads to phase singularity (PS). PS is defined as a point at which phase is undefined or un-definable, but its neighbor points have phases in a range from $-\pi$ to $\pi$.

Figure 13:
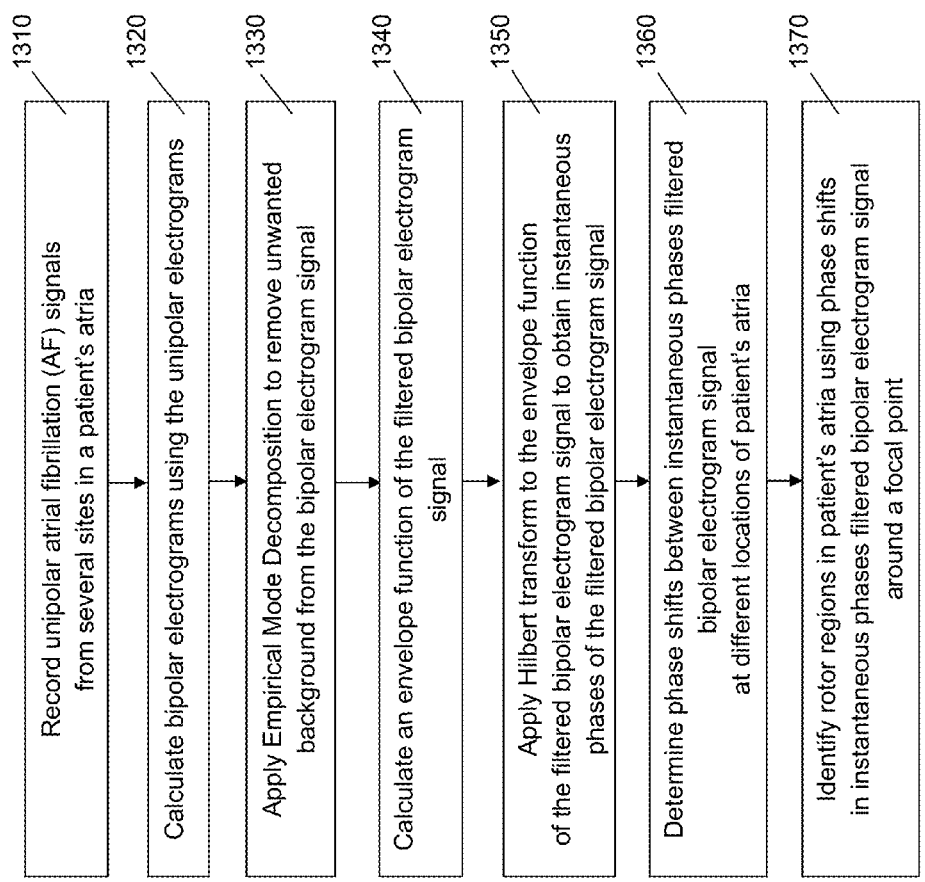
FIG. 13 is a flow diagram for identifying critical rotor regions in patient's atria in some embodiments of the present invention.

Referring to FIG. 13, unipolar electrograms are recorded different locations of a patient's atria (step 1310). The recordation can be conducted by a multi-probe-type catheter. Bipolar electrograms are then calculated using the unipolar electrograms recorded at adjacent sites (step 1320). Bipolar electrogram is the difference between two unipolar electrograms recorded at two adjacent sites. The distance between the two sites is typically within a few millimeters. Clinically, bipolar electrogram is preferred because the subtraction step can cancel out common noises such as interferences from power line. The bipolar signal is, however, biphasic, which can its phase increasing from 0 to $2\pi$ within very short time duration (<25 msec) which is far below the true firing period. Though far-field (remote) signals in the bipolar recording are more attenuated, and the bipolar recording is more sensitive to local effects, the very weak far field oscillations can still seriously contaminate the phase function. To address these issues, we proposed to estimate the phase from the envelope function of bipolar signal. The fibrillation electrogram is pre-processed by band-pass filter designed with pass band 40-250 Hz 40-order Kaiser Window (step 1325). The envelope function is extracted from the filtered signal by one-dimensional order-statistic filtering (step 1328).

Prior to calculation of its phase function, the signal is preprocessed to remove unwanted trends using a linear high pass filter or subtracting the signal by a nonlinear polynomial fitting trend. Although single linear trends are easily removed by utilizing a traditional polynomial fitting, the heterogeneous non-stationarity in physiological signals usually has multiple different local trends, which makes it difficult to filter those trends out using traditional methods.

In the present disclosure, Empirical Mode Decomposition (EMD) is used to remove the unwanted background in the envelope function of the bipolar electrogram signal to obtain an envelope function of the filtered bipolar electrogram signal (step 1330). In EMD, a time series data y(t) is decomposed into a number of intrinsic modes of oscillations:

$$y(t) = \sum_{k=1}^{k=n} c_k(t) + r_n \quad (4)$$

in which $c_k(t)$ is termed intrinsic mode functions (IMFs). The IMFs are decomposed sequentially from the original time series by identifying intrinsic undulations at different time scales. The IMFs with frequency distributions below 1.5 Hz were removed.

Figure 14:
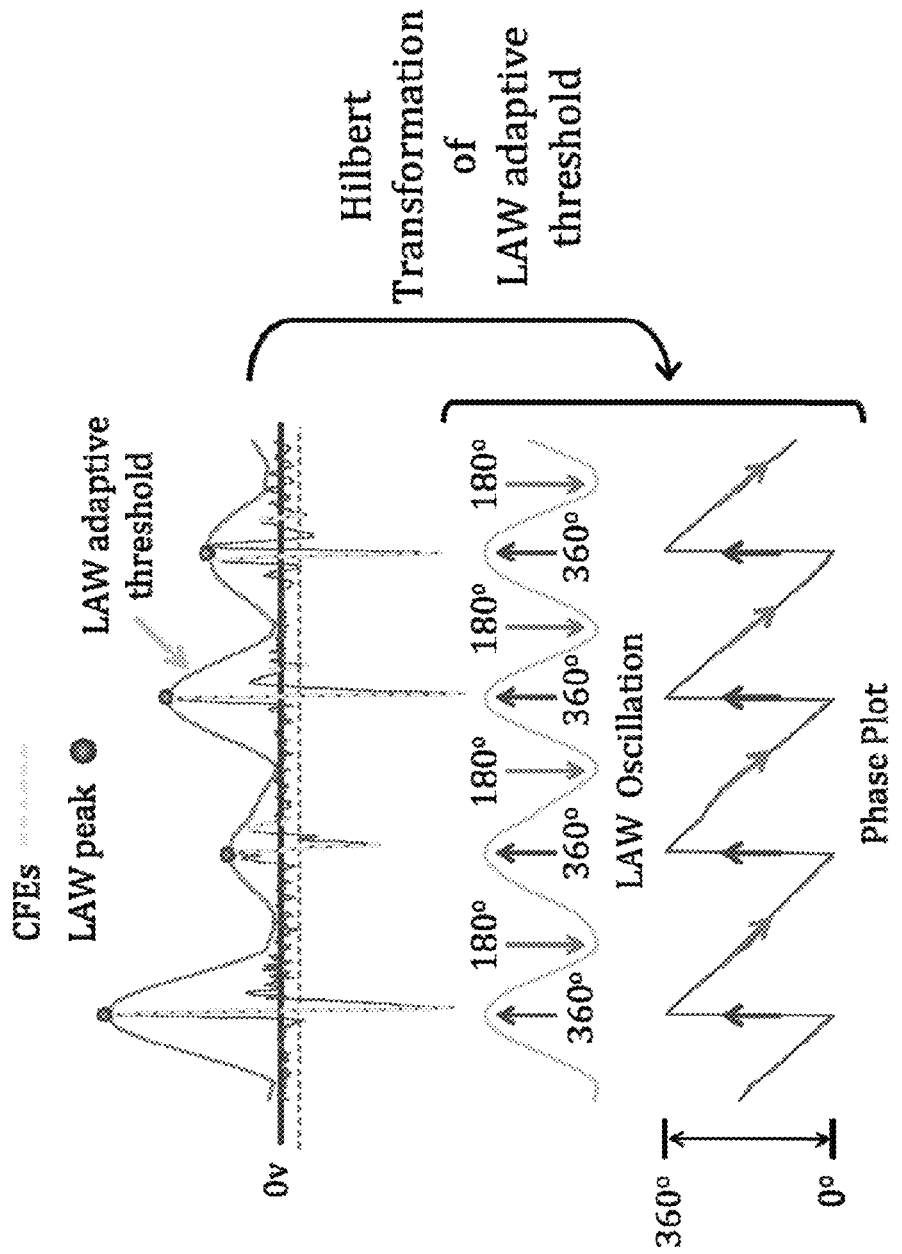
FIG. 14 shows the envelope extraction and phase angle acquisition.

After noises and residual trends are removed from the bipolar electrogram signal, an envelope function of the filtered signal is calculated (step 1340). Hilbert transform is next applied to the envelope function of the filtered signal to obtain instantaneous phases of the to filtered bipolar electrogram signal (step 1350), as shown in FIG. 14. For a time series s(t), its Hilbert transform is defined as $$\tilde{s}(t) = \frac{1}{\pi} P \int \frac{s(t')}{t - t'} dt' \quad (5)$$

wherein P denotes the Cauchy principal value. Hilbert transform has an apparent physical meaning in Fourier space: for any positive (negative) frequency f, the Fourier component of the Hilbert transform $\tilde{s}(t)$ at this frequency f can be obtained from the Fourier component of the original signal s(t) at the same frequency f after a 90° clockwise (counterclockwise) rotation in the complex plane, e.g., if the original signal is $\cos(\omega t)$, its Hilbert transform becomes $\cos(\omega t - 90°) = \sin(\omega t)$. For any signal s(t), the corresponding analytic signal can be constructed by combination of the original signal and its Hilbert transform:

$$S(t) \equiv s(t) + i\tilde{s}(t) = A(t)e^{i\phi(t)} \quad (2)$$

where A(t) and $\phi(t)$ are the instantaneous amplitude and instantaneous phase of s(t), respectively. For each pair of electrodes, the instantaneous phases of s(t) in phase plot correlate with LAW oscillations in the bipolar electrogram signal, as shown in FIG. 14.

Figures 15A, 15B:
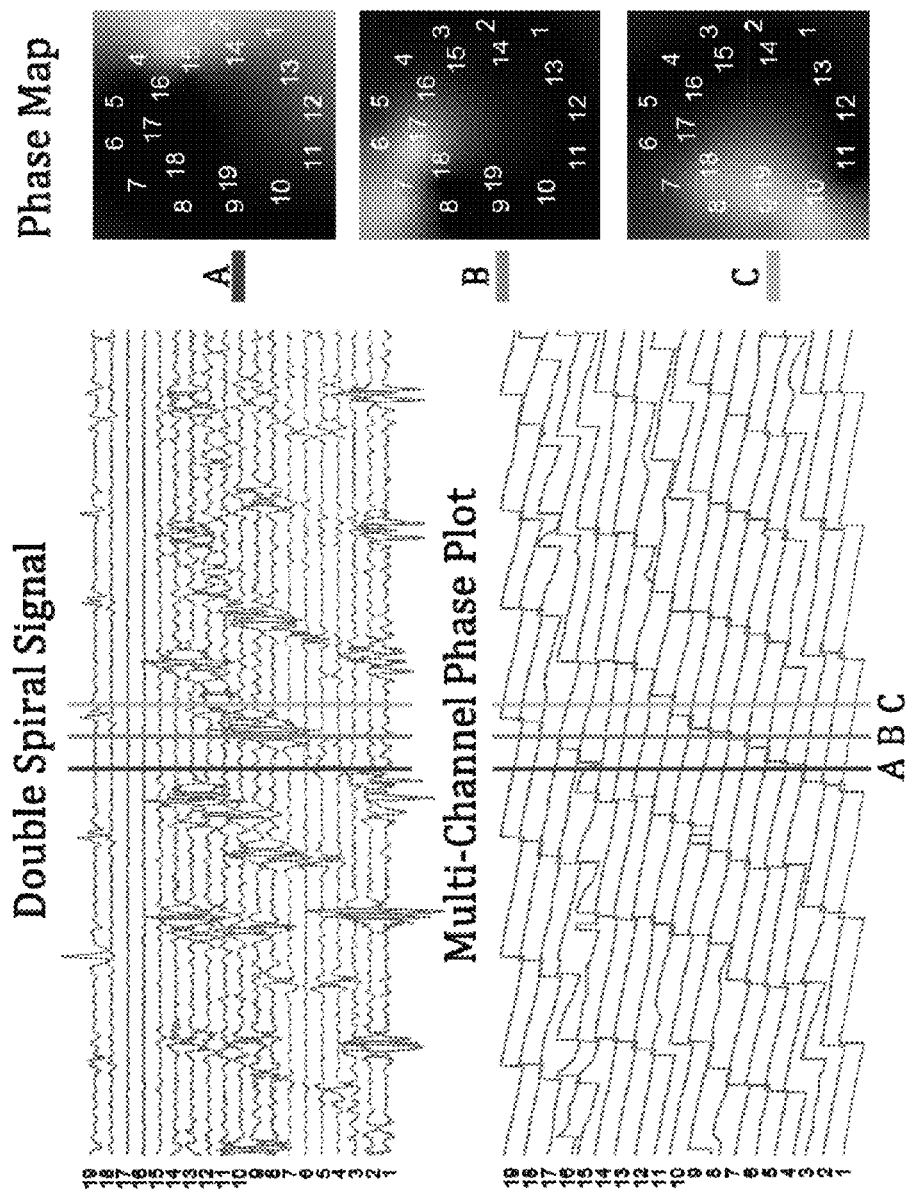
FIG. 15A shows exemplified time sequences of phase angle variations at different probing sites.
FIG. 15B shows exemplified real time phase maps at different times in the time series of phase signals in FIG. 15A.

FIG. 15A shows time sequences of phase angle variations at different probing sites. In FIG. 15B, the three images A, B, C are real time phase maps marked with locations of 19 electrodes. The time series of phase data of the 19 electrodes are plotted in FIG. 15A with double spiral signal plotted on the upper left and regular phases plotted on the lower left. The phases in adjacent locations are shifted (or travels) from the 1st electrode to 15th electrode, resulting a total 360 degree phase shift (step 1360), which represents a full rotation in the counter clock direction in the images A, B, C in FIG. 15B. The three images A, B, C are snapshots of phase shifts at the three times A, B, C indicated in the time series in FIG. 15A. The light regions in FIG. 15B indicate areas where a full 360 degree rotation has occurred (step 1360), which identify locations of the rotors in patient's atria (step 1370). The rotor regions in patient's atria are identified using instantaneous phases filtered bipolar electrogram signal (step 1370).

Figure 16A:
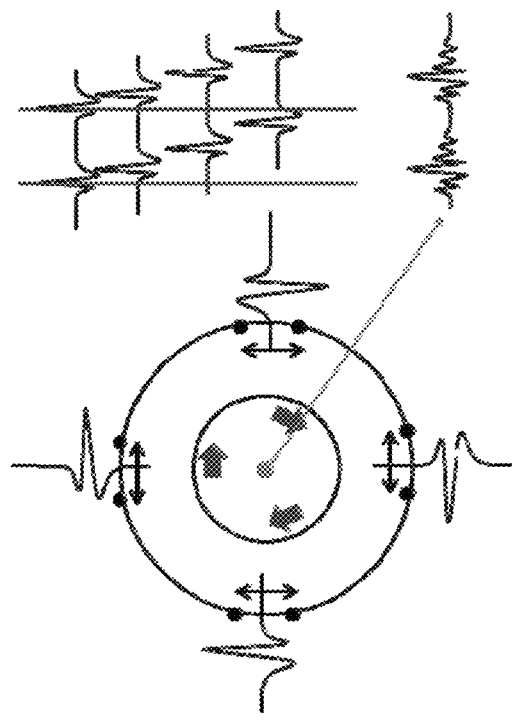
FIG. 16A illustrates the presence of a rotor in a patient's atria.

The real time phase maps such as shown in FIG. 15B can be used to confirm 4 propagation types: rotor, focal point, traveling wave, and random fraction. For example, referring to FIG. 16A, the phase shifts at different positions at substantially the same distance to a center point are calculated relative to the phase at the center point (step 1360). In FIG. 16A, phases are calculated at four positions (the top, right, below, and left positions) along a circle around the center point. The rotation of the phase shifts around the center point shows the presence of a rotor in a patient's atria (step 1370).

Figure 16B:
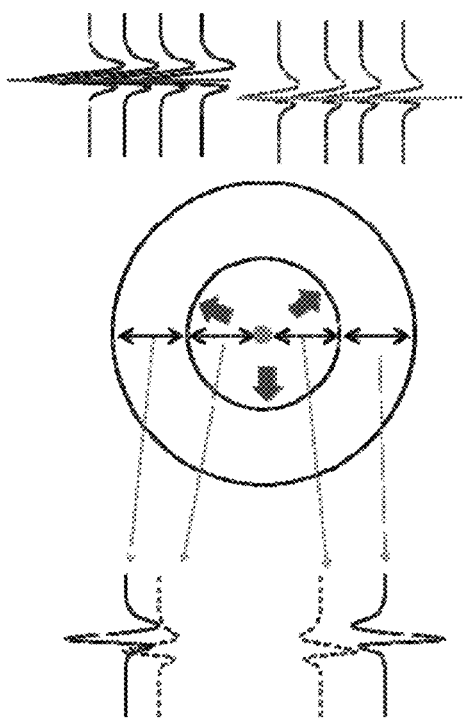
FIG. 16B illustrates the focal point in the probing region in a patient's atria.

FIG. 16B illustrates the focal point in the probing region in a patient's atria. In the phases are measured at different radial distances from a central focal point. The phases are found to be shifting away from the central focal point. Similarly, in some cases, the phases may be shifting inward to the focal point.

Validation

Figure 17:
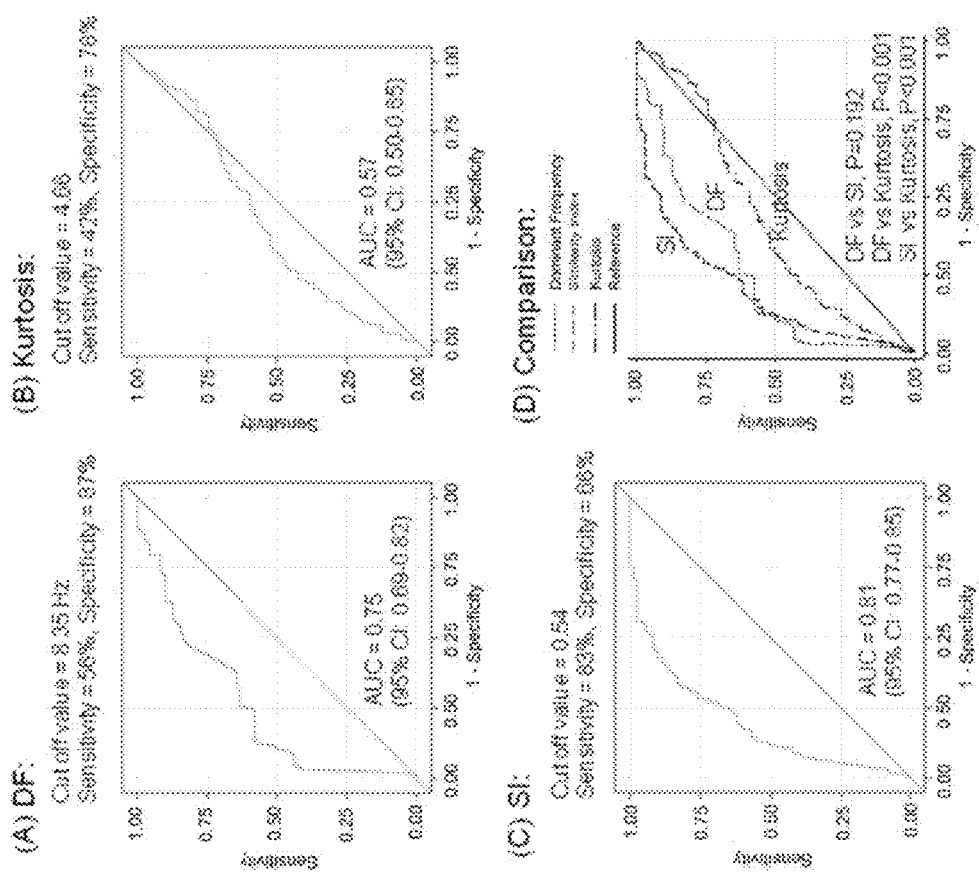
FIG. 17 illustrates exemplified receiver operating characteristic (ROC) curve analysis that displays the optimal thresholds for detecting a small-radius reentry based on the algorithm of the (A) dominant frequency, (B) kurtosis, (C) similarity index, and (D) comparison of the pairwise AUCs for the DF, kurtosis, and SIs.
Figure 18:
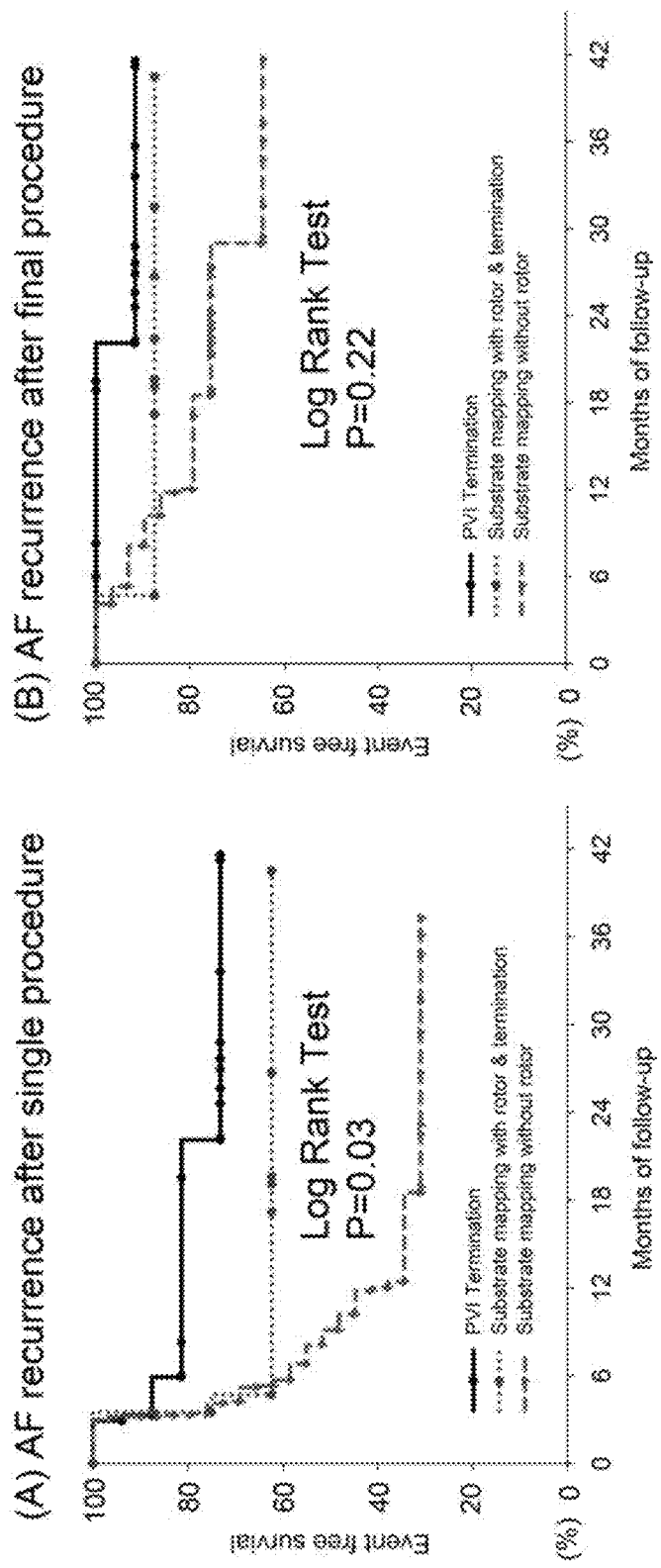
FIG. 18 illustrates exemplified Kaplan-Meier curves demonstrating the freedom of atrial arrhythmia recurrence after a single (A) and multiple procedures (B). AF indicates atrial fibrillation; and pulmonary vein isolation (PVI).

Overall 9 rotors were identified in 8 patients (1.1 per patient). The rotor regions were characterized by a higher mean DF, kurtosis and a lower mean FI compared with the outside-rotor regions in patients with AF termination and atrial substrate without rotors (p<0.05). As shown in Table 1, the electrograms with a higher DF, kurtosis, and SIs were associated with the rotor regions in the multivariate Generalized estimating equation (GEE) model (p<0.05). Other signal characteristics such as the degree of the CFEs and electrogram voltage did not predict the rotors. The AUCs (Area under curve) of the DF and SI were higher than that of the kurtosis (P<0.001, FIG. 17). After a mean follow-up duration of 23.1 (18.6-29.3) months, the recurrence rate among the PVI termination, rotor group, and nonrotor group of any atrial arrhythmia after the first ablation procedure was 25%, 38%, and 69% (Log-rank test, P=0.03) and after the final ablation procedure was 6%, 13%, and 28%, respectively (P=0.22; FIG. 18). Patients without rotors had a more complex ablation strategy to achieve freedom of atrial arrhythmias after multiple procedures. The number of ablation procedures was larger in the rotor group than in the nonrotor group (1.86±0.89 versus 1.25±0.46 procedures per patient; P=0.1).

TABLE 1

Electrogram characteristics in different types of patients

| Variables | With Rotors | | Without Rotors Atrial substrate | Univariate analysis by GEE | Multivariate analysis by GEE |
| --- | --- | --- | --- | --- | --- |
| | Inside rotor† (N = 71) | Outside rotor† (N = 394) | without rotors (N = 2935) | P value, OR (95% CI) | P value, OR (95% CI) |
| Dominant frequency (Hz) | 8.59 ± 1.87* | 6.07 ± 1.39 | 6.97 ± 1.62 | <0.001, 1.38 (1.18-1.60) | <0.001, 1.38 (1.19-1.60) |
| Harmonic index | 0.41 ± 0.05* | 0.40 ± 0.04 | 0.39 ± 0.05 | 0.62, 1.16 (0.65-2.08) | — |
| Kurtosis | 4.50 ± 2.60* | 4.08 ± 2.08 | 3.79 ± 1.50 | 0.007, 1.10 (1.03-1.18) | 0.029, 1.09 (1.01-1.17) |
| Electrogram voltage (mV) | 0.68 ± 0.44 | 71 ± 0.63 | 0.65 ± 0.67 | 0.80, 1.02 (0.86-1.22) | — |
| Fractionation interval (ms) | 64.4 ± 15.9* | 75.5 ± 20.4 | 70.5 ± 20.5 | 0.003, 0.97 (0.96-0.99) | 0.129, 0.99 (0.98-1.00) |
| Similarity index | 0.62 ± 0.08* | 0.50 ± 0.08 | 0.51 ± 0.10 | <0.001, 2.22 (1.90-2.58) | <0.001, 1.77 (1.56-2.02) |

*P < 0.01, when compared to the corresponding points outside the rotors and patients without rotors by post-Hoc analysis; OR = odd ratio; as presented by per increment of 0.1 in similarity index and harmonic index.
†Area covered by a small-radius re-entry in the primary CFE area is defined as the "inside-rotor" sites and the remaining area is termed as the "outside-rotor" sites.

It should be understood that the above described systems and methods are compatible to with different configurations and variations without deviating from the spirit of the present invention. For example, AF signals are not limited to surface ECG waveforms.

What is claimed is:

1. A computer-assisted method for quantitative characterizing atrial fibrillation in a patient, comprising:
   recording unipolar atrial fibrillation (AF) signals from multiple sites in a patient's atria using a plurality of probes;
   calculating bipolar electrograms using unipolar AF signals recorded at adjacent sites by an analyzer in connection with the probes, wherein the analyzer includes an analog-to-digital converter;
   extracting an envelope function from the filtered bipolar electrograms using one-dimensional order statistic filtering by the analyzer;
   applying Empirical Mode Decomposition to remove a background from the envelope function of the bipolar electrogram signal to obtain an envelope function of the filtered bipolar electrogram signal;
   applying Hilbert transform to the envelope function of the filtered bipolar electrogram signal to obtain a time series of instantaneous phases of the filtered bipolar electrogram signal;
   displaying a spatial diagram of the instantaneous phases in the patient's atria at one or more times in the time series on a display in connection with the analyzer, wherein the spatial diagram is based on the multiple sites in a patient's atria probed by the plurality of probes;
   highlighting a graphical area in the spatial diagram of the instantaneous phases to show movements of the graphical area on the display;
   demonstrating a rotational movement of the graphical area to show existence of a rotor region in the spatial diagram of the instantaneous phases obtained from the patient's atria, comprising:
      calculating a map of the instantaneous phases in the envelope function of the filtered bipolar electrogram signal in the patient's atria; and
      calculating phase shifts at different positions around a center point relative to a phase at the center point, wherein the different positions are at substantially the same distance to the center point;
   identifying the rotor region in the patient's atria if the phase shifts at the different positions rotates around the center point; and
   overlaying the rotor region on a map of the patient's atria on the display to locate the rotor region in the patient's atria to allow therapy to be delivered to the located rotor region in the patient's atria, which increases the rate of successful procedural AF terminations.

2. The computer-assisted method of claim 1, wherein the step of applying Empirical Mode Decomposition comprises:
   decomposing a time series of the envelope function of the bipolar electrogram signal into a number of intrinsic mode functions; and
   removing intrinsic mode functions having frequency distributions below 1.5 Hz to obtain a filtered bipolar electrogram signal.

3. The computer-assisted method of claim 1, further comprising:
   plotting time series of the instantaneous phases in the envelope function of the filtered bipolar electrogram signal recorded at the multiple sites in the patient's atria; and identifying the rotor region in the patient's atria based on phase shifts at the multiple sites.

4. The computer-assisted method of claim 1, further comprising:

preprocessing the bipolar electrograms using a band-pass filter before the step of extracting.

* * * * *